United States Patent [19]

Katz

[11] Patent Number: 5,177,070
[45] Date of Patent: Jan. 5, 1993

[54] METHOD OF TREATING PHYSIOLOGIC MALE ERECTILE IMPOTENCE

[75] Inventor: Richard Katz, Teaneck, N.J.

[73] Assignee: Ciba-Geigy Corporation, Ardsley, N.Y.

[21] Appl. No.: 793,039

[22] Filed: Nov. 15, 1991

[51] Int. Cl.$^5$ ............................................. A61K 31/55
[52] U.S. Cl. .................................................. 514/215
[58] Field of Search ........................................ 514/215

[56] References Cited

U.S. PATENT DOCUMENTS 4,663,318  5/1987  Davis ................................. 514/215

OTHER PUBLICATIONS

Chemical Abstracts 112:112096y (1990).
D. Paskov and D. Traikov: Treatment of Psychogenic form of Sexual Astenia with Nivalin Suremenna Meditsina, vol. 25 No. 12, pp. 30–34, 1974.
Harrison's 10th. Ed. pp. 240–243.

Primary Examiner—Leonard Schenkman
Attorney, Agent, or Firm—Irving M. Fishman; Karen G. Kaiser

[57] ABSTRACT

Method of treating male erectile impotence secondary to physiological dysfunction by administering, preferably orally, the cholinergic agent galanthamine or a pharmaceutically acceptable salt thereof, most preferably the hydrobromide salt, in amounts of preferably 10–20 mg based on the hydrobromide, up to three to four times a day.

11 Claims, No Drawings

METHOD OF TREATING PHYSIOLOGIC MALE ERECTILE IMPOTENCE

FIELD OF THE INVENTION

The present invention relates to the use of galanthamine free base, galanthamine hydrobromide and related pharmaceutically acceptable salts (hereinafter galanthamine), a cholinergic agent, in the treatment of male erectile impotence secondary to physiological dysfunction.

BACKGROUND OF THE INVENTION

Male sexual dysfunction, impotence, can result from a number of distinct problems. These include loss of desire or libido, the inability to maintain an erection, premature ejaculation, lack of emission, and inability to achieve an orgasm. Frequently, more than one of these problems present themselves simultaneously. The conditions maybe secondary to other disease states (typically chronic conditions), the result of specific disorders of the urogenital system or endocrine system, secondary to treatment with pharmacological agents (e.g. antihypertensive drugs, antidepressant drugs, antipsychotic drugs, etc.) or the result of psychiatric problems.

The present invention deals with the inability to obtain or maintain an erection which is due to physiologic factors. The present invention does not deal with psychogenically caused erectile impotence. Galanthamine has been reported as useful in the treatment of psychogenic form of sexual asthenia in Savr. Med. (Bulgaria), 1974, 25/12 (30-34).

Physiologic erectile impotence differs from psychogenic erectile impotence in significant ways and one can readily separate the two types. From early childhood through at least the eighties, erections occur during normal sleep and is known as nocturnal penile tumescence or NPT. This happens during rapid eye movement (REM) sleep and the total NPT time per night averages about 100 min. These erections continue to occur in patients having the psychogenic form of erectile impotence while they do not occur in men with physiological causes for their impotence. Therefore, the simple observation that erectile function is present during sleep indicates that a psychogenic cause rather than a physiologic cause is at work. Alternative means for a differential diagnosis between the psychogenically and physiologically mediated condition include the use of a strain gauge with recorder or wrapping with perforated paper and noting failure to rupture the perforations.

According to Harrison's *Principles of Internal Medicine*, 10th Ed. pp. 240-243 (1983), medical therapy for impotence has included androgens (useful only in hypogonadal men), bromocriptine or surgical treatment (for prolactin secreting pituitary tumor), surgery for aortic obstruction, and implantation of prosthetic devices. As stated above, galanthamine, a cholinergic drug believed potentially to be useful for Senile Demetia of the Alzheimer's Type (SDAT), has been reported to alleviate the psychogenic form of erectile impotence.

As far as the present inventor is aware there is no suitable therapeutic substance available for the treatment of physiologic male erectile impotence. Recently, certain tetrahydrobenzindole serotonin agonists (such as those in EP-A 392,768) have been alleged to be of value in improving sexual function, particularly male potency. U.S. Pat. No. 4,530,920 mentions peptides useful in hypogonadal conditions and impotence; however, it appears that the activity of the peptide disclosed there is related to its androgen stimulation. As such, it would not be expected to be of any value in conditions where hypogonadism is not at issue.

Physostigmine has been used to obtain an ejaculation from paraplegic men (Andrologia 20 (4):311-3, July-August 1988). Neostigmine has been used intrathecally to obtain a sample from a paraplegic male for artificial insemination purposes (Paraplegia 24 (1):32-7, 1986 Feburary).

The United States Pharmacopoeia, 9th Edition lists papaverine and phentolamine as useful in impotence. Papaverine is an opium alkaloid and it relaxes smooth muscle in the ureter and blood vessels. Phentolamine is an adrenergic inhibitor, while physostigmine and neostigmine are cholinergic agents.

OBJECT OF THE INVENTION

It is an object of the invention to provide a method of treating physiologic male erectile impotence with a therapeutic agent.

It is a further object of the invention to provide a method of treating physiologic male erectile impotence without the attendant side effects of the currently available agents indicated for this condition.

SUMMARY OF THE INVENTION

The present invention is a method of treating non-psychogenic forms of male erectile impotence in a male animal in need of such treatment comprising administering to such male animal an erectile impotence treating therapeutically effective amount of galanthamine, or a pharmaceutically acceptable salt thereof.

DETAILED DESCRIPTION OF THE INVENTION

Galanthamine use in SDAT is set forth in U.S. Pat. No. 4,663,318 (the '318 Patent), which is incorporated herein by reference. The present invention is the administration of galanthamine to a patient with physiologically mediated, rather than psychogenically mediated, male erectile impotence.

The compound can be formulated as set forth in the '318 Patent as well as be administered in amounts and routes as set forth there. The compound is most advantageously administered in amounts of from 1-100 mg, preferably 2-75 mg, more preferably about 4 to about 70 mg, per dose. The dosage unit is most advantageously tablets or capsules, but may be any other convenient dosage form. While the preferable route of administration is oral, any other convenient mode of administration may be used. Most preferably, the compound is administered in amounts of 5-25 mg and even more preferably about 10 to about 20 mg per dose. The compound is most advantageously administered from 1 to 4 times a day, most preferably three times a day. The above dosages are approximate for an adult human male of approximately 70 kg and are based on galanthamine hydrobromide. Equivalent amounts using the free base or other salts can be readily determined by those of ordinary skill. For use with human males of significantly different weight or with non-human animals, the drug should be administered in the range of about 0.015 to about 1.5 mg/kg, preferably 0.03 to about 1 mg/kg, more preferably 0.075 to 0.225 mg/kg per dose which is administered from 1 to 4 times a day.

The invention can also be practiced with sustained release dosage delivery forms in which case each dosage unit will have the appropriate multiples of the effective amounts set forth above so as to be able to deliver an effective amount of galanthamine or a pharmaceutically acceptable salt thereof for the intended delivery period. For example, a once a day sustained delivery dosage form intended to deliver drug over the entire 24 hour period may contain the equivalent of up to 4 of the doses indicated above. Variations on this theme will be apparent to those of ordinary skill in this area and are considered to be within the scope of the invention.

Pharmaceutically acceptable salts of galanthamine include, but are not limited to, the hydrochloride, hydrobromide, sulfate, phosphate, fumarate, citrate, methylsulfate, and methiodide. Other acid addition salts suitable for pharmaceutical use will be apparent to those of ordinary skill.

The following Examples are intended to further detail specific embodiments of the invention without limiting the scope of the specification or claims.

EXAMPLE 1

A human male patient suffering from a senile loss of erectile function in conjunction with normal aging and its sequelae is given 20 mg of galanthamine hydrobromide orally three times a day to alleviate erectile dysfunction.

EXAMPLE 2

A human male patient receiving the β-adrenergic blocker propranolol for hypertension and suffering from concomitant erectile failure secondary to the antihypertensive therapy is given 15 mg of galanthamine hydrobromide three times a day to restore erectile capacity.

I claim:

1. A method for the treatment of physiologic male erectile impotence in a male animal in need of such treatment comprising administering to such male animal a physiologic male impotence treating effective amount of galanthamine or a pharmaceutically acceptable salt thereof.

2. The method of claim 1 wherein said effective amount is about 1 to about 100 mg/dose.

3. The method of claim 2 wherein said effective amount is about 4 to about 70 mg/dose.

4. The method of claim 3 wherein said effective amount is about 5 to about 25 mg/dose.

5. The method of claims 4 wherein said effective amount is about 10 mg to about 20 mg/dose.

6. The method of claim 1 wherein said effective amount is about 0.015 mg/kg to about 1.5 mg/kg of said animal.

7. The method of claim 6 wherein said effective amount is about 0.075 mg/kg to about 0.375 mg/kg of said animal.

8. The method of claim 7 wherein said effective amount is about 0.15 mg/kg to about 0.3 mg/kg of said animal.

9. The method of claim 2 wherein said galanthamine of a pharmaceutically acceptable salt thereof is administered to said animal up to 4 times a day.

10. The method of claim 6 wherein said galanthamine or a pharmaceutically acceptable salt thereof is administered to said animal up to 4 times a day.

11. The method of claim 1 wherein said animal is a human.

* * * * *

UNITED STATES PATENT AND TRADEMARK OFFICE
CERTIFICATE OF CORRECTION

PATENT NO. : 5,177,070
DATED : January 5, 1993
INVENTOR(S) : Richard Katz

It is certified that error appears in the above-identified patent and that said Letters Patent is hereby corrected as shown below:

Claim 5, column 4, line 16 "method of claims 4" should read --method of claim 4--

Claim 9, column 4, line 28 "of a pharmaceutically" should read --or a pharmaceutically--

Signed and Sealed this

Seventh Day of December, 1993

Attest:

Attesting Officer

BRUCE LEHMAN
Commissioner of Patents and Trademarks